US00PP21723P2

(12) United States Plant Patent
Zaiger et al.

(10) Patent No.: US PP21,723 P2
(45) Date of Patent: Feb. 22, 2011

(54) INTERSPECIFIC TREE NAMED 'NEWROOT-1'

(50) Latin Name: *Prunus salicina×Prunus avium*
Varietal Denomination: Newroot-1

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 0 days.

(21) Appl. No.: 12/655,906

(22) Filed: Jan. 11, 2010

(51) Int. Cl.
*A01H 5/00* (2006.01)

(52) U.S. Cl. ..... Plt./180

(58) Field of Classification Search ..... Plt./180
See application file for complete search history.

*Primary Examiner*—Annette H Para

(57) ABSTRACT

A new and distinct variety of interspecific rootstock tree. Its novelty consist of the following combination of desirable features that are unique in a new rootstock tree when growing cherries (*Prunus avium*). The new interspecific rootstock was grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Provides earlier production of fruit when growing cherries.
2. Reduces the mature cherry tree height compared to the standard cherry rootstock 'Mahaleb' (non-patented) or 'Mazzard' (non-patented).
3. Increase the number of rootstocks available for cherries.

1 Drawing Sheet

Botanical classification: Interspecific *Prunus* species.

BACKGROUND OF THE VARIETY

In the field of plant genetics, we conduct an extensive and continuing plant-breeding program including the organization and asexual reproduction of orchard trees and of which; plums, peaches, nectarines, apricots, cherries, almonds, interspecifics and rootstocks are exemplary. It was against this background of our activities that the present variety of interspecific rootstock tree was originated and asexually reproduced by us in our experimental orchard located near Modesto, Stanislaus County, Calif.

PRIOR VARIETIES

Among the existing varieties of rootstocks, plum and cherry trees which are known to us and mentioned herein are; 'Atlas' Rootstock (U.S. Plant Pat. No. 8,913), 'Viking' Rootstock (U.S. Plant Pat. No. 8,912), 'Amazon' Plum (U.S. Plant Pat. No. 2,043), 'Friar' Plum (non-patented), 'Craig's Crimson' Cherry (U.S. Plant Pat. No. 7,320), 'Royal Rainier' Cherry (U.S. Plant Pat. No. 10,790) and the non-patented cherry varieties 'Black Tartarian', 'Stella', 'Bing', 'Lapins' the proprietary seedling selection of plum '85EG395' and the proprietary cherry seedling selection '5.5GK110'.

STATEMENT REGARDING FEDERALLY SPONSORED RESEARCH AND DEVELOPMENT

Not applicable.

ORIGIN OF THE VARIETY

The new and distinct variety of interspecific tree, [*Prunus salicina×Prunus avium*] was originated by us in our experimental orchard located near Modesto, Calif. as a first generation cross between two proprietary seedling selections, the seed parent '85EG395' crossed with pollen from '5.5GK110'. The (85EG395) originated from crosses between 'Amazon' Plum (U.S. Plant Pat. No. 2,043) and the 'Friar' Plum (non-patented). The cherry pollen parent (5.5GK110) originated from an open pollinated proprietary cherry seedling of unknown parentage. A large number of these seedlings were budded on older trees of 'Nemagaurd' Rootstock (non-patented) to induce earlier and larger branch growth to be used for rootstock cuttings to determine the asexual reproduction of these seedlings from cuttings. The seedlings that developed the most desirable rooting ability were selected for propagation to various varieties of cherries (*Prunus avium*). One such selection with desirable rooting ability, which is the present variety, was tested by budding and grafting and found to be compatible with various cherries 'Craig's Crimson' (U.S. Plant Pat. No. 7,320, 'Royal Rainier' (U.S. Plant Pat. No. 10,790), and the non-patented cherry varieties 'Van', 'Black Tartarian', 'Stella' 'Bing', 'Lapins', also budded to approximately 20 proprietary cherry seedling selections, and was selected in 2000 for additional asexual propagation and commercialization.

ASEXUAL REPRODUCTION OF THE VARIETY

Asexual reproduction of the new and distinct variety of interspecific rootstock tree was by dormant rootstock cutting, as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new and distinct variety of interspecific rootstock tree (*Prunus salicina*×*Prunus avium*), which is medium in size, upright in growth and the cuttings from the tree have the ability to develop roots similar to 'Atlas' Rootstock (U.S. Plant Pat. No. 8,913) and 'Viking' Rootstock (U.S. Plant Pat. No. 8,912) when planted directly into the field. The present new variety of interspecific rootstock is further characterized by the rapid rooting of its cuttings, allowing for spring budding of cherries (*Prunus avium*), producing few or any root or trunk suckers. In comparison to the primary standard rootstocks for production of commercial cherry trees 'Mazzard' (non-patented) and 'Mahaleb' (non-patented), we observed a dwarfing effect (more with 'Mazzard' than 'Mahaleb') and 2 to 3 years earlier in fruit production.

PHOTOGRAPH OF THE VARIETY

The accompanying color photographic illustration shows typical specimens of the foliage and fruit of the present new interspecific rootstock variety. The illustration shows the upper and lower surface of the leaves, an exterior and sectional view of a single fruit divided in its suture plane to show flesh color, pit cavity and the stone remaining in place. The photographic illustration was taken shortly after being picked from a 10 year old tree and the colors are as nearly true as is reasonably possible in a color representation of this type.

DESCRIPTION OF THE VARIETY

The following is a detailed botanical description of the new variety of interspecific rootstock tree, its flowers, foliage and fruit, as based on observations of 10 year old specimens grown near Modesto, Calif., with color in accordance with Munsell Book of Color.

Tree:

*Size.*—Medium, tree pruned severely each winter to induce proper new growth for rootstock cuttings. Average spread 3.0 m. Average height 3.5 m, varies with different cultural practices.

*Vigor.*—Moderate vigor, cut back in dormant season to 1 to 1.5 m each year to induce new growth for rootstock cuttings.

*Form.*—Upright.

*Branching habit.*—New growth from cut back branches have approximately 30° angle by end of next season.

*Productivity.*—Productive, fruit has no commercial value.

*Bearer.*—Regular.

*Fertility.*—Self sterile.

*Density.*—Dense, numerous branching from cut back trees increase density and provides numerous cuttings.

*Hardiness.*—Tree grown in USDA Hardiness Zone 9. Hardy in all stone fruit growing areas of California.

Trunk:

*Size.*—Medium, circumference 47 cm, measured 24.5 cm above ground on a 10 year old tree.

*Stocky.*—Medium.

*Surface texture.*—Medium shaggy, increases with age of tree.

*Color.*—Varies from 10YR 4/2 to 2.5Y 2/2.

Branches:

*Size.*—Medium, trees branches cut back each dormant season for additional rootstock cuttings.

*Surface texture.*—New growth relatively smooth. Mature growth medium rough.

*Lenticels.*—Number — 19 in 25.8 sq cm surface area. Average length 3.8 mm. Average width 1.4 mm. Color varies from 10YR 6/8 to 10YR 6/10.

*Color.*—New growth varies from 5GY 4/8 to 7.5YR 3/4. Old growth varies from 10YR 3/4 to 10YR 2/2, varies with age of growth.

Leaves:

*Size.*—Small to medium. Average length 64.6 mm. Average width 38.3 mm.

Form.—Ovate.

*Apex.*—Acuminate.

*Base.*—Cunate.

*Margin.*—Serrate.

*Thickness.*—Medium.

*Surface texture.*—Upper surface relatively smooth, only slightly indented over midrib and leaf veins, glabrous. Lower surface relatively smooth, small ridges created by midrib and pinnate venation, glabrous.

*Petiole.*—Average length 11.7 mm. Average width 1.0 mm. Color varies from 2.5GY 5/4 to 5GY 5/6. Longitudinally grooved. Surface — glabrous.

*Glands.*—Type — globose. Size — small. Average length 0.5 mm. Average diameter 0.2 mm. Number varies from 1 to 3, average number 2. Located primarily on base of leaf blade. Color varies from 2.5GY 6/6 to 5GY 6/6.

*Color.*—Upper surface varies from 5GY 3/6 to 7.5GY 3/4. Lower surface varies from 5GY 4/4 to 7.5GY 4/4. Midrib color varies from 2.5GY 8/4 to 5GY 8/4.

*Venation.*—Pinnately veined.

Flower buds:

*Size.*—Small. Average length 8.7 mm. Average diameter 4.9 mm.

*Hardiness.*—Hardy in all stone fruit growing areas of California.

*Form.*—Conical, becoming slightly elongated just before opening.

*Pedicel.*—Average length 7.0 mm. Average width 0.6 mm.

*Color.*—N 9.5/ (white).

*Number of buds per spur.*—Average number 7, varies from 4 to 13.

Flowers:

*Blooming period.*—Date of First Bloom Feb. 25, 2009. Date of Petal Fall Mar. 7, 2009, varies slightly with climatic conditions.

*Size.*—Small to medium. Average height 10.1 mm. Average diameter 21.7 mm.

*Petals.*—Normally 5, alternately arranged to sepals. Size — small to medium. Average length 10.2 mm. average width 9.5 mm. Form — obovate, narrows at point of attachment. Margin — sinuate. Color N 9.5/ (white).

*Sepals.*—Normally 5, alternately arranged to petals. Size — small. Average length 3.3 mm. Average width 2.9 mm. Shape — ovate, somewhat triangular. Margin — entire. Both upper and lower surfaces glabrous. Color — upper surface varies from 5GY 6/8 to 5GY 5/6. Lower surface varies from 5GY 5/4 to 5GY 4/4.

*Stamens.*—Average number per flower 33, varies from 31 to 36. Average length 7.8 mm. Filament color N 9.5/ (white). Anther color varies from 5Y 8/10 to 5Y 7/10.

*Pollen.*—Self sterile. Color varies from 2.5Y 7/10 to 5Y 7/12.

*Pistil.*—Number — normally 1. Surface — glabrous. Average length 10.0 mm. Position of stigma — even with anthers. Color varies from 2.5GY 8/6 to 2.5GY 7/6.

*Fragrance.*—Heavy.

*Color.*—N 9.5/ (white).

*Number flowers per flower bud.*—Average 3, varies from 1 to 5.

*Pedicel.*—Average length 7.0 mm. Average width 0.6 mm. Color varies from 2.5GY 6/6 to 2.5GY 5/8.

Fruit:

*Maturity when described.*—Firm ripe, no commercial value.

*Date of fruit maturity.*—Jun. 3, 2009, varies slightly with climatic conditions.

*Size.*—Small. Average diameter axially 30.7 mm. Average transversely in suture plane 35.1 mm. Average weight 25.6 grams, varies slightly with fertility of the soil and climatic conditions.

*Form.*—Globose.

*Suture.*—Nearly smooth.

*Ventral surface.*—Nearly smooth.

*Apex.*—Slightly retuse.

*Base.*—Flat, varies from flat to slightly retuse.

*Stem cavity.*—Rounded. Average depth 2.7 mm. Average diameter 5.1 mm.

Stem:

*Size.*—Small. Average length 9.7 mm. Average diameter 1.0 mm.

*Color.*—Color varies from 2.5GY 5/4 to 2.5GY 5/6.

Flesh:

*Ripens.*—Evenly.

*Texture.*—Firm.

*Fibers.*—Few, small.

*Firmness.*—Firm.

*Aroma.*—Very slight.

*Amydgalin.*—Undetected.

*Eating quality.*—Poor, no commercial value.

*Flavor.*—Slightly tart.

*Juice.*—Lacking.

*Brix.*—Average Brix 14.0°, varies slightly with amount of fruit per tree and climatic conditions.

*Color.*—Varies from 5Y 9/6 to 5GY 8.5/6. Pit cavity varies from 2.5Y 7/8 to 2.5Y 6/10.

Skin:

*Thickness.*—Medium.

*Surface.*—Smooth.

*Pubescence.*—Glabrous.

*Tendency to crack.*—Slight.

*Bloom.*—Wanting.

*Color.*—Ground color varies from 2.5Y 8.5/8 to 5Y 9/6. Surface color varies from 5R 3/10 to 5R 2/8.

*Tenacity.*—Tenacious to flesh.

*Astringency.*—None.

Stone:

*Type.*—Semi-cling.

*Size.*—Small to medium. Average length 16.8 mm. Average width 14.7 mm. Average thickness 9.0 mm.

*Form.*—Ovoid.

*Base.*—Flat.

*Apex.*—Slightly pointed. Average length 0.2 mm.

*Surface.*—Very slightly pitted throughout.

*Sides.*—Unequal, one side extending further from suture plane.

*Ridges.*—Very small ridge, extends from base to apex.

*Tendency to split.*—None.

*Color.*—Varies from 7.5YR 5/6 to 10YR 5/6.

Kernel:

*Size.*—Small. Average width 8.0 mm. Average length 11.3 mm. Average depth 5.7 mm.

*Form.*—Ovate.

*Viability.*—Viable, complete embryo development.

*Skin.*—Varies from 2.5Y 8.5/4 to 5Y 9/4.

Use: Rootstock for tree size control and precocious fruit of cherries (*Prunus avium*).

Keeping quality: Not evaluated, fruit of non-commercial value.

Shipping quality: Not evaluated, fruit of non-commercial value.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific rootstock tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of rootstock tree, substantially as illustrated and described.

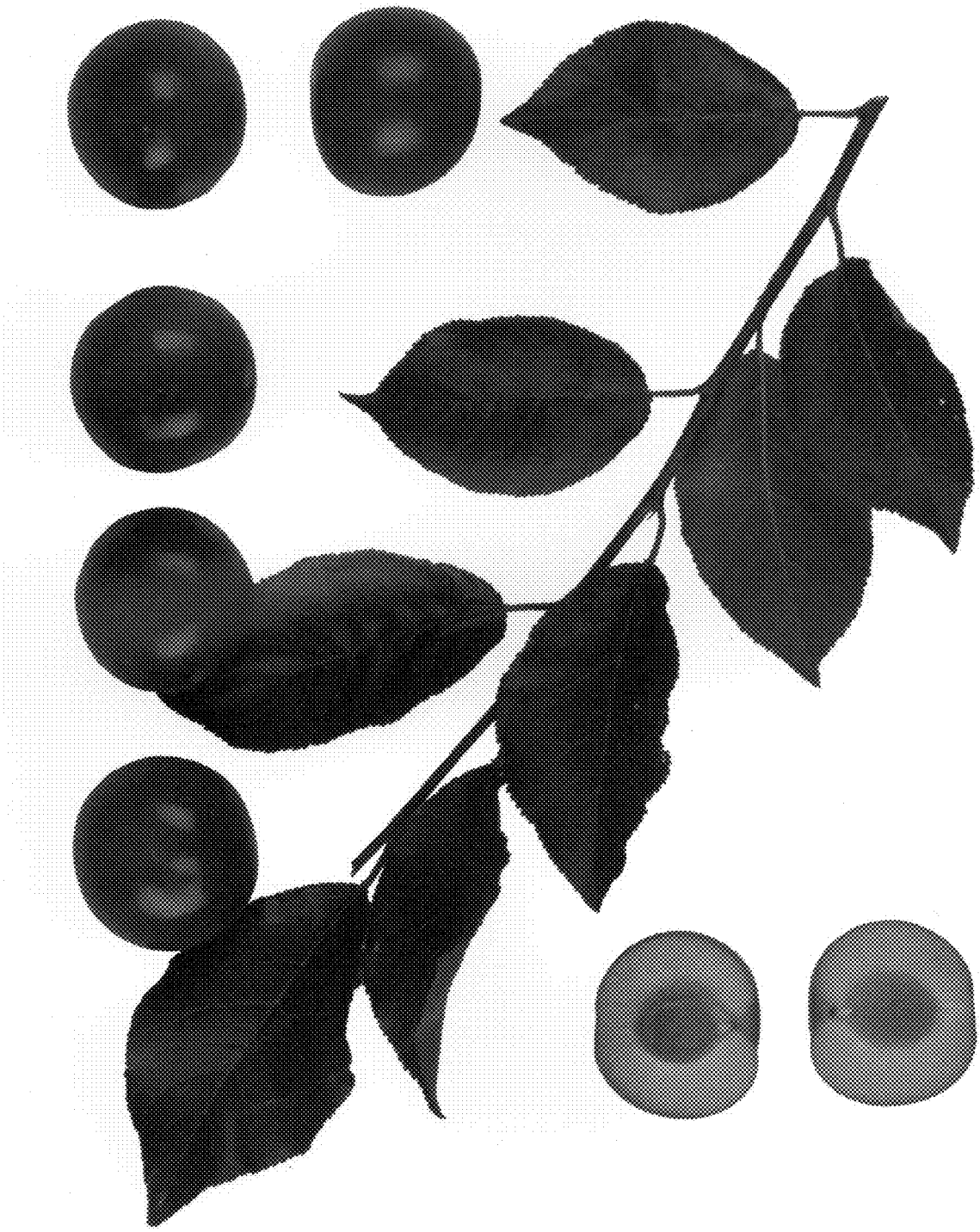

* * * * *